US00PP09503P

United States Patent [19]

Schumann

[11] Patent Number: Plant 9,503

[45] Date of Patent: Apr. 9, 1996

[54] GERANIUM PLANT NAMED 'FISCHIC'

[75] Inventor: Ingeborg Schumann, Albstadt, Germany

[73] Assignee: Florfis AG, Binningen, Switzerland

[21] Appl. No.: 360,346

[22] Filed: Dec. 21, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium named Fischic, particularly characterized by the combined features of intense bluish pink flower color, semi-double flower type, light green foliage with weak zonation, compact plant habit, and medium early flower response.

2 Drawing Sheets

The present invention comprises a new and distinct cultivar of geranium, botanically known as *Pelargonium peltatum l'Hert*, commonly referred to as ivy geranium, and referred to by the cultivar name Fischic.

Fischic is a product of a planned breeding program which has the objective of creating new geranium cultivars with pink flower color and bushy, well-branched plant habit.

Fischic was originated from a hybridization made by inventor Ingeborg Schumann in a controlled breeding program in Galdar, Gran Canaria, Spain in 1987. The female parent was Isidel, a cultivar having purplish red semi-double flowers, long peduncles and vigorous growth. Fischic was derived from a chance seedling of the parent variety.

Fischic was discovered and selected as one flowering plant within the progeny of the stated cross by Ingeborg Schumann in 1988 in a controlled environment in Galdar, Gran Canaria, Spain.

The first act of asexual reproduction of Fischic was accomplished when vegetative cuttings were taken from the initial selection in autumn 1989 in a controlled environment in Galdar, Gran Canaria, Spain, by, or under the supervision of, Ingeborg Schumann.

Horticultural examination of plants grown from these cuttings initiated in May 1990, and continuing thereafter, has demonstrated that the combination of characteristics as herein disclosed for Fischic are firmly fixed and are retained through successive generations of asexual reproduction.

Fischic has not been observed under all possible environmental conditions. The phenotype may vary significantly with variations in environment such as temperature, light intensity and daylength without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fischic, which, in combination, distinguish this geranium as a new and distinct cultivar:

1. Intense bluish pink flower color.
2. Semi-double flower type.
3. Light green leaves with weak zonation.
4. Compact growth habit.
5. Medium early flower response.

Of the many commercial cultivars known to the present inventor, the most similar in comparison to Fischic are Rigi and the parent cultivar Isidel. Reference is made to attached Chart A which compares certain characteristics of Fischic to those same characteristics of Rigi. In general comparison to Rigi, Fischic has a pink flower color with more bluish tint, much more compact plant habit, smaller flowers and umbels, and smaller leaves. With respect to Isidel, the pink flower color of Fischic is somewhat lighter and has more bluish tint, the flowers of Fischic are more uniformly shaped, and its plant habit is more compact.

The accompanying color photographic drawings show typical flower and foliage characteristics of Fischic, with colors being as true as possible with illustrations of this type. The photo on Sheet 1 is a plant of Fischic in a hanging basket. The photograph on Sheet 2 is a plant of Fischic in a pot, with the umbels and foliage being shown in greater detail.

In the following description, color references are made to The Royal Horticultural Society Colour Chart. The color values were determined indoors in May from plants grown indoors in Hillscheid, Federal Republic of Germany.

Classification:

*Botanical.*—A hybrid of the species *Pelargonium peltatum l'Hert.*

*Commercial.*—Ivy geranium, cv., Fischic.

INFLORESCENCE

Umbel:

*Shape.*—Almost semi-spherical.
*Average diameter.*—85 mm.
*Average depth.*—45 mm.
*Peduncle length.*—130 mm.
*Pedicel length.*—24 mm.
*Pedicel color.*—Green and partly dark red.
*Number of flowers per umbel.*—8–9.

Corolla:

*Average diameter.*—50 mm.
*Form.*—Semi-double.
*Number of petals.*—11.
*Number of petaloids.*—2–3.
*Color (General tonality from a distance of three meters).*—Bluish pink.
*Color of upper petals.*—67B.
*Color of lower petals.*—67B.
*Markings on upper petals.*—Dark red veins.
*Color of lower surface of petals.*—66C.
*Color of sepals.*—Light green, largest sepal has slight red coloring.
*Number of sepals.*—5–6.

Bud:

*Shape.*—Elliptical.
*Color (adaxial).*—Medium green.
*Color (abaxial).*—Red or rose red.

Reproductive organs:

*Androecium.*—5–7 fertile anthers, pink filaments, yellow-orange pollen.

*Gynoecium.*—5–6 lobed stigma, pink style and stigma.

Spring flowering response period: In Hillscheid, Federal Republic of Germany, in 1993 plants had on average 1.1 flowers opened 15 1 weeks after planting of unrooted cuttings (pinched plants).

Outdoor flower production: The flower count in 1993 in Hillscheid, Federal Republic of Germany was about 50 umbels per plant for May through August observaton period. This is more or less average but due to the compact habit of Fischic, the umbels are relatively closer together thereby making the plant appear more floriferous.

Durabiltiy: Shatter resistance good.

Seed: Seed set has not been observed.

PLANT

Foliage:

*Form.*—Ivy-shaped.

*Margin.*—Entire.

*Size of leaf.*—90–100 mm.

*Color of upper surface.*—Light green, approximately 137D.

*Color (zonation).*—Brown 166A. The zonation is comparatively weak and forms a small ring near the base of the leaf. The zonation is usually best visible on younger leaves and young plants, or under outdoor conditions with low night temperatures. During the summer months, few mature leaves show a distinct zonation.

*Tolerance of Botrytis.*—Average.

General appearance and form:

*Internode length.*—15–30 mm.

*Branching pattern.*—1.2 branches per week.

*Length.*—45 cm (in September, 35-week-old plants).

CHART A

| CHARACTERISTIC | FISCHIC | RIGI |
|---|---|---|
| Flower color, upper petals | 67B | 57C |
| Number of petals | 7–11 | 6–8 |
| Plant length | 45 cm | 100 cm |
| Distinctness of zonation | Weak | Medium to strong |

It is claimed:

1. A new and distinct cultivar of geranium plant named Fischic, as illustrated and described.

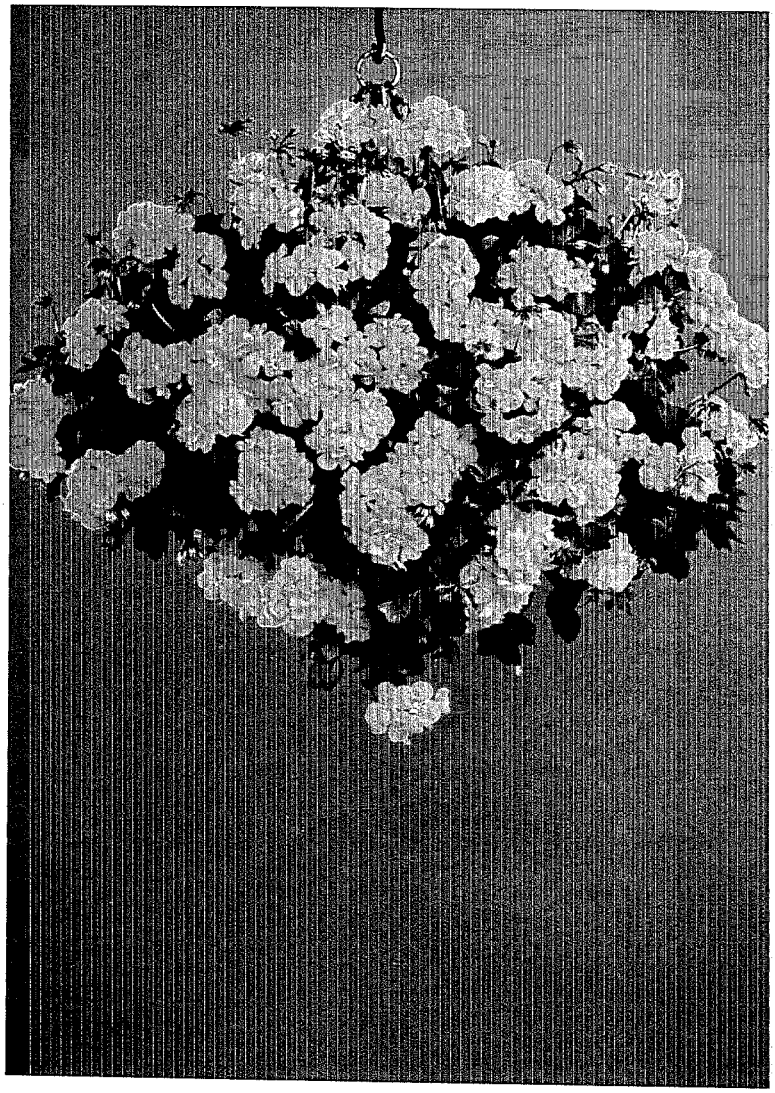

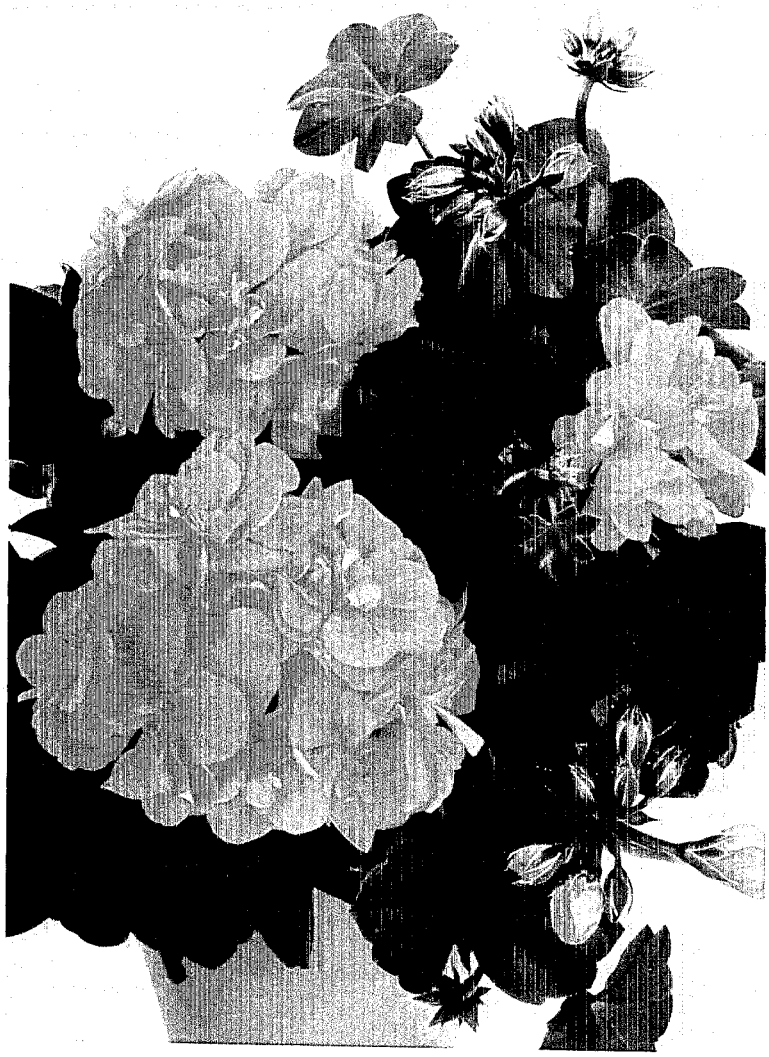

* * * * *